(12) United States Patent
Maschke (10) Patent No.: US 8,750,964 B2
(45) Date of Patent: Jun. 10, 2014

(54) DEVICE FOR DETERMINING THE POSITION OF A MEDICAL INSTRUMENT

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 1312 days.

(21) Appl. No.: 11/526,250

(22) Filed: Sep. 22, 2006

(65) Prior Publication Data

US 2007/0066882 A1 Mar. 22, 2007

(30) Foreign Application Priority Data

Sep. 22, 2005 (DE) .......................... 10 2005 045 362

(51) Int. Cl.
*A61B 5/05* (2006.01)
(52) U.S. Cl.
USPC .......................................................... 600/424
(58) Field of Classification Search
USPC .................................................. 600/407, 424
See application file for complete search history.

(56) References Cited

U.S. PATENT DOCUMENTS

| | | | |
|---|---|---|---|
| 5,365,943 A | 11/1994 | Jansen | |
| 5,391,199 A | 2/1995 | Ben-Haim | |
| 5,540,959 A | 7/1996 | Wang | |
| 5,570,770 A | 11/1996 | Baaten et al. | |
| 5,596,996 A | 1/1997 | Johanson et al. | |
| 5,638,819 A | 6/1997 | Manwaring et al. | |
| 5,752,513 A | 5/1998 | Acker et al. | |
| 5,827,997 A | 10/1998 | Chung et al. | |
| 5,849,355 A * | 12/1998 | McHenry .................... 427/79 |
| 5,928,149 A * | 7/1999 | Habraken ..................... 600/425 |
| 6,152,878 A | 11/2000 | Nachtomy et al. | |
| 6,233,476 B1 | 5/2001 | Strommer et al. | |
| 6,263,230 B1 * | 7/2001 | Haynor et al. ................ 600/424 |
| 6,298,261 B1 | 10/2001 | Rex | |
| 6,366,799 B1 | 4/2002 | Acker et al. | |
| 6,506,972 B1 | 1/2003 | Wang | |
| 6,673,999 B1 | 1/2004 | Wang et al. | |
| 6,788,967 B2 | 9/2004 | Ben-Haim et al. | |
| 6,813,512 B2 | 11/2004 | Aldefeld et al. | |
| 2001/0031919 A1 | 10/2001 | Strommer et al. | |

(Continued)

FOREIGN PATENT DOCUMENTS

CN 1668254 A2 9/2005
DE 40 37 586 A1 5/1992

(Continued)

OTHER PUBLICATIONS

Biophan Technologies, Inc., "Delivering Visionary Medical Technology", [online], http://www.biophan.com/shielding.php, Retrieved on Sep. 22, 2006, pp. 1-2.

(Continued)

*Primary Examiner* — Tse Chen
*Assistant Examiner* — Mark Remaly (57) ABSTRACT

Device for determining the position of at least one medical instrument with a position sensor system inserted into the body of a patient for an examination using imaging examination equipment, in particular X-ray equipment, wherein the device has a computing unit, in which at least one piece of examination equipment specific information limiting the possible spatial positions of the medical instrument during the examination is stored, wherein the computing unit is designed to determine the position in a limited position area of the possible spatial positions and according to the limiting examination equipment specific information.

10 Claims, 4 Drawing Sheets

(56) References Cited

U.S. PATENT DOCUMENTS

| | | | |
|---|---|---|---|
| 2002/0049375 A1 | 4/2002 | Strommer et al. | |
| 2004/0034297 A1 | 2/2004 | Darrow et al. | |
| 2004/0127894 A1 | 7/2004 | Eick et al. | |
| 2004/0176683 A1* | 9/2004 | Whitin et al. | 600/424 |
| 2004/0199072 A1* | 10/2004 | Sprouse et al. | 600/424 |
| 2007/0066889 A1* | 3/2007 | Boese et al. | 600/424 |

FOREIGN PATENT DOCUMENTS

| | | |
|---|---|---|
| DE | 42 15 901 A1 | 8/1993 |
| DE | 43 35 301 C1 | 12/1994 |
| DE | 198 27 460 A1 | 12/1998 |
| DE | 198 52 467 A1 | 7/1999 |
| DE | 696 03 265 T2 | 3/2000 |
| DE | 695 14 238 T2 | 5/2000 |
| DE | 693 27 436 T2 | 8/2000 |
| DE | 100 51 244 A1 | 5/2002 |
| DE | 694 28 525 T2 | 5/2002 |
| EP | 0 456 103 A2 | 11/1991 |
| EP | 0 993 804 A1 | 4/2000 |
| EP | 1 034 738 B1 | 9/2000 |
| WO | WO 02/13709 A1 | 2/2002 |
| WO | WO 2004/052225 A2 | 6/2004 |

OTHER PUBLICATIONS

Jullus H. Grollman, Jr., David Borger and Charles Moler, Simultaneous Electronic and Small Format Photofluorographic Angiography, Radiology, vol. 123, Jun. 1977, pp. 791-793.

P. Heintzen, "Videodensitometry with Pulsed Radiation", In Roentgen—Cine and Videodensitometry, Stuttgart, Georg Thieme Verlag, 1971, pp. 46-56.

P. Kok, "An experimental stereo-television x-ray system", Medica Mundi, vol. 15, 1970, pp. 39-42.

* cited by examiner

DEVICE FOR DETERMINING THE POSITION OF A MEDICAL INSTRUMENT

CROSS REFERENCE TO RELATED APPLICATIONS

This application claims priority of German application No. 10 2005 045 362.7 DE filed Sep. 22, 2005, which is incorporated by reference herein in its entirety.

FIELD OF INVENTION

The invention relates to a device for determining the position of at least one medical instrument with a position sensor system inserted into the body of a patient for an examination using imaging examination equipment, in particular X-ray equipment, and an associated imaging examination equipment and a method.

BACKGROUND OF THE INVENTION

Vascular diseases such as cardiac infarction rank among the most frequent diseases resulting in death. They are caused by diseases of the blood vessels where plaque deposits have resulted in a narrowing or "blocking" of the blood vessels. One treatment possibility is to extend the constrictions of, for example, the coronary vessels with a so-called "balloon catheter", to which end, a guide wire is passed through the vascular system into the area of the constriction that is to be treated. A guide catheter can then be moved over the guide wire to the ostium of the coronary artery, wherein, in the so-called "over-the-wire" method, a balloon catheter is introduced over the guide wire inside the guide catheter. The balloon at the distal end of the catheter is then inflated and the stenosis widened. Medical instruments are also inserted into the body of the patient in a similar way in the case of other diseases.

As a rule, treatments of this kind are carried out using X-ray control after the administration of a contrast medium. The medical instruments used, such as, for example, catheters or guide wires, are equipped with a position sensor system, which is in most cases magnetic or electromagnetic and which has in addition external components such as transmitters or receivers outside the body, in order thus to locate the instrument in the body of the patient and to track and monitor the treatment. The monitoring is used, for example, to prevent the instrument from causing damage to the vascular systems.

Positioning or locating systems of this kind currently involve computational effort that cannot be neglected, in order to determine the actual position, as for the human body, for example, as described in DE 42 15 901 A1, the model of an infinite monochromatic conductive half-space is assumed. Thus the search area that a data processing system runs through for the location in order to actually determine the position, is infinite, so that the reconstruction time until images are actually present can be very long depending on the available computer system. Therefore, considerable computing resources are required and also the treatment may be unnecessarily drawn out due to delays.

SUMMARY OF INVENTION

The object underlying the invention is thus to specify a device for position determination improved in this respect.

In order to achieve this object, a device of the type named in the introduction is provided according to the invention, which device has a computing unit in which at least one piece of examination equipment specific information limiting the possible spatial positions of the medical instrument during the examination is stored, wherein the computing unit is designed for position determination of the possible spatial positions in a limited position area according to the limiting examination equipment specific information.

Thus, according to the invention, in contrast to previous position sensor systems, an infinite space or a infinite half-space are not used as search area for the position of the medical instrument, but at least one piece of information is stored in a computing unit, which information is able to limit the position of the medical instrument. This is possible, for example, because information on the geometrical structure of the imaging examination equipment is stored, in which equipment the patient and hence the catheter or guide wire or another medical instrument must be located. The computing unit that carries out the position determination accesses this one piece of information or several pieces of information, by retrieving said information from its memory or from a memory available for access. Now in order to perform the actual position determination, the computing unit uses the information available to limit the search area, which corresponds to the position area of the possible spatial positions, by which the computational effort for the position determination can be clearly reduced.

Advantageously, several pieces of information of this kind limiting the position area of the possible spatial positions are included in the calculation for locating the instrument. Using this, it is possible, for example, to achieve a real-time location using an electromagnetic and/or a magnetic position sensor system.

The imaging examination equipment can be X-ray equipment, but can also be a computed tomography device or a magnetic resonance device. In addition, the inventive device can be used with ultrasound systems or with positron emission tomography as well as with the SPECT method (Single Photo Emission Computed Tomography) or similar equipment.

The length and/or width and/or a minimum and/or maximum height of a patient table and/or an imaging unit, in particular from an X-ray source, and/or the length and/or other dimensions of the medical instrument and/or information as to the spatial arrangement and/or as to the movement limitations of the examination equipment can be stored in the computing unit as limiting examination equipment specific information.

By way of example, it is inevitably the case that the patient is lying on a patient table or couch during treatment to remove arteriosclerotic plaque, so that the information about the table dimensions, i.e. the width or length of the table, can be used to limit the position determination to this area. In addition, the maximum lower position of the patient is preset by the height of the table top, and the maximum upper position when an X-ray control system is used is preset by the lowest height the X-ray can still reach. In addition the length or the extension of the medical instrument inserted, such as, for example, of a catheter or of a guide wires, can be used to limit the search area for calculating the position of the instrument.

There may be other information available on the spatial arrangement of the examination equipment, for example, on the structural limitations in the area above the couch as a result of other apparatus or suchlike. These can also be retrieved and taken into consideration by the computing unit, in order to limit the location area. Likewise the possible options or limitations of movement of the couch or those of a radiation source for recording X-ray images or suchlike that may exist can be used to limit position area of the possible spatial positions. In this way, the computational effort and the required reconstruction time for control exposures can be reduced using position data.

The computing unit can be part of a collision computer system and/or designed to access a collision computer system and/or to process the data stored in such a system in order to determine limiting examination equipment specific information. In a collision computer system appliance movement limitations with respect, for example to the movement of the image recording unit, are fixed in such a way that the patient on the patient couch will not knock against the image recording devices or is restricted by said devices or similar. Thus in a collision computer system are stored the basic limits for the numerous movement possibilities in modern systems, for example for carrying out angiographic exposures. Therefore, the computing unit, which establishes the position area for the position determination, can also be part of such a collision computer system or advantageously at least be able to access such a collision computer system in order to retrieve the data that already exists there and which limits the position area. If necessary, the computing unit can be physically separated from the collision computer system, but in such a case, it is of advantage that the computing unit is at least capable of processing the data available in such a system to determine from that limiting and examination equipment specific information. This information is then stored in the computing unit or at least held in the short-term in order to limit the position area for the position determination of the medical instrument inserted into the body of the human or animal patient. These measures distinctly reduce the search area in which the medical instrument is searched for during the position determination.

In addition the computing unit can be designed to recognize possible magnetic field changes in the area of the examination equipment and/or for position determination according to the possible magnetic field changes.

If a treatment just involves an X-ray control, then a constriction or the vascular diameter can only be represented as a two dimensional silhouette. Likewise in angiographic X-ray images, the guide wire or a catheter or other medical instruments are represented as two-dimensional superimposed images. Moreover the medical instrument and the tissue are shown variably well in the X-ray image. However, it is desirable to have a good spatial representation of all objects, which allows optimized determination of the spatial arrangement in the patient and where in addition a lower radiation dose is sufficient. In as far as spatial location is provided in the case of medical catheters, for example in combination with sensors for emitting intravascular ultrasound, there is the disadvantage that the generally used systems work on the principle of electromagnetic locating and react sensitively to magnetic field changes in the environment and these can influence the precision of the position determination negatively. Negative influence on the magnetic fields used for locating can, moreover, be caused by other medical instruments and appliances such as instrument trolleys or suchlike. Moreover the transmitting units of the magnetic locating systems may adversely affect the image processing chain.

In order to tackle this problem, according to the invention additional measures enable the computing unit to recognize possible magnetic field changes, in particular all magnetic field changes around the examination equipment and to input these field changes to, for example, an error correction computing unit, which allows for these field changes when reconstructing images from position sensors. This allows the location accuracy to be increased. If necessary the error correction computing unit can be a part of the computing unit for position determination, so that both the position area limitation and the corrections with respect to magnetic field changes can be included directly into the position determination to be carried out. Thus the position determination is carried out in a limited position area of the possible spatial positions of the medical instruments of examination, and according to the possible magnetic field changes.

The computing unit for detecting the field changes and/or the position determination according to the field changes can be designed to set at least one time interval and/or a clocking cycle for a trigger signal and/or the operation of an imaging unit and/or the readout of a detector system and/or the activation of the position sensor system and/or the updating of a on-screen display of the image data recorded.

With X-ray equipment, for example, one could also make it possible set the time intervals for a possible delay or a possible advance in the timing of the radiation release, of the reading out of the X-ray detector, which can be, for example, a silicon detector, a CCD detector (Charge Coupled Device detector) or a television tube, or the activation, for example, of the electromagnetic locating system. This makes it possible for the position sensor system designed electromagnetically or otherwise to be individually customized to suit the X-ray equipment of a specific manufacturer. For example, it is possible for the position determination of the medical instrument to be carried out as a function of an updating of an on-screen display of the image data recorded, in order to thus suppress artifacts that could appear on the screen due to magnetic signals from the locating system. Thereby, the time intervals or clocking cycles can be set by accessing a system of rules or data stored in a storage device of the computing unit for position determination or for detecting possible magnetic field changes. This can be a database system or similar.

Further in setting several time intervals and/or clocking cycles, the computing unit can be designed to at least partially synchronize the setting of the time intervals and/or clocking cycles, in particular for synchronized setting taking into consideration at least one delay and/or one advance. Thus synchronization is practical to the effect that, for example, a display such as a TFT or similar is not updated during the time when a magnetic locating is active, or that the magnetic locating is not activated or switched off during the updating period. In addition, it is useful if a CCD detector or a TV detector, is, if necessary, read out with a certain delay after the X-rays have been switched off, and in addition are read out at times when the magnetic locating is not active. Possible magnetic field changes are thus allowed for in the image reconstruction, the time intervals and clocking cycles are synchronized in such a way that there can be no crossovers of interfering signals. To this end, a detector can be read out after the X-rays have been turned off or after the X-rays have been turned off with a certain delay, while the magnetic locating prior to the X-rays being switched on is active, so that there is no interference of individual processes. If need be the magnetic locating can also be active during an X-ray impulse, if a corresponding delay of the detector readout ensures that this will not cause any interference from the magnetic locating.

The imaging unit, in particular an X-ray source, may be operated continuously and/or pulsed. Thus the X-rays can be switched on or off again at intervals of some 10 milliseconds. Alternatively, the X-rays can remain on for a longer period of time after a trigger signal for the electronic data processing, the detector being read out at specific intervals during this time or a magnetic or electromagnetic locating being activated several times, whereby locating and reading out is carried out at different times.

When pulsed X-rays are used, it is possible to select any frequency desired, for example, in a range of 0.5-200 pulses per second. In the case of pulsed X-rays up to 15 pulses per second, one can achieve, for example, a dose saving, whereas, with higher frequencies one can achieve improved image blur.

In addition, it is possible for the locating system or position sensor system to be activated several times between the readout cycles of an X-ray detector, this, for example, directly after a readout and with a certain delay again before the next detector readout.

The computing unit can be designed to access and/or to allow for, magnetic field paths of the examination equipment that have been stored in particular in a control unit, and/or to access and/or to allow for field states that have been stored, especially in a calibration unit, where the examination equipment is of different operating modes.

Thus, advantageously, after the installation of examination equipment or unit with appropriate measuring means, the magnetic field changes are recorded that are caused by navigation magnets of a navigation system, so that said changes do not falsify the readings of the locating system from the transmitters and receivers. This data is stored in a system control and consulted as stored field line paths in the reconstruction of magnetic locating vectors so as to avoid errors of measurement.

A calibration unit enables static and dynamic magnetic field states to be stored in different function stages e.g. when moving a C-arm system, and to be taken into consideration during signal evaluation and correction computation for image conversion. To this end, when the examination equipment is being installed or commissioned, a locating test is performed on a known test body, running through all the positions of the X-ray system that can occur and the associated magnetic field distortions are recorded. Advantageously the calibration unit hereby exchanges data with the collision computer or is linked to the inventive computing unit or represents a part of this computing unit so that the calibration unit data can be taken into consideration in the position determination and detection of magnetic field changes.

The signal lines of the position sensor system can be designed with at least partial shielding against magnetic fields or against interference fields, in particular with a thin film coating of conductive nanoparticles. Thus magnetic shielding is achieved using nanotechnology or using another shielding technology, in order to limit the influence of magnetic interference.

In addition, the invention relates to imaging examination equipment, which is designed with a device for determining the position of at least one medical instrument with a position sensor system, in particular a magnetic or electromagnetic position sensor system, as described above. Thus with the imaging examination equipment, which is based, for example, on a C-arm system for producing X-ray images, it is possible to achieve rapid and accurate position determination of medical instruments by limiting the position area of the possible spatial positions and also allowing and compensating for magnetic interference fields. Allowance can be made in particular for those interference fields caused by movements of the medical examination equipment, such as, for example, a table movement, a movement of the C-arm or movements of other medical instruments and appliances in the vicinity of the examination equipment or inside the examination equipment. This makes a faster and more precise position determination possible.

In addition the signal lines and/or function units of the examination equipment, in particular a detector system, can be designed with at least partial shielding against magnetic fields, in particular with a thin film coating made of conductive nanoparticles. This shields the physiological signals or the image signals and the signal processing and conditioning against the magnetic fields of the transmitting antennae of the position sensor system and other possible magnetic interference fields.

Moreover, the invention relates to a method for determining the position of at least one medical instrument inserted into the body of a patient for an examination with imaging examination equipment, in particular X-ray equipment. The method is carried out using a device for determining position with a magnetic position sensor system that has a computing unit, in which there is stored at least one piece of examination equipment specific information limiting the possible spatial positions of the medical instrument during the examination, wherein the computing unit is designed to determine the position according to the limiting examination equipment specific information and in a limited position area of the possible spatial positions. Thus, in the inventive method the search area for the position of the catheter or other medical instrument that has corresponding position sensor devices such as transmitter or receiver, for example, in the region of its tip, is clearly limited. It is no longer an infinite space that is searched, geometric and other default settings of the examination equipment such as, for example, the position of the patient table in the room and its dimensions are included from the start as limiting factors in the calculation of the position. The device can be designed as required in the way described above. Thus it is possible in the scope of the inventive method in particular to detect all the magnetic field changes surrounding an examination device, it being possible for these magnetic field changes to be input to an error correction computing unit so that they can be taken into consideration in the image reconstruction and hence to increase the precision of the locating.

BRIEF DESCRIPTION OF THE DRAWINGS

Other advantages and details of the invention are shown by the following exemplary embodiments and drawings, in which.

DETAILED DESCRIPTION OF INVENTION

Figure 1:
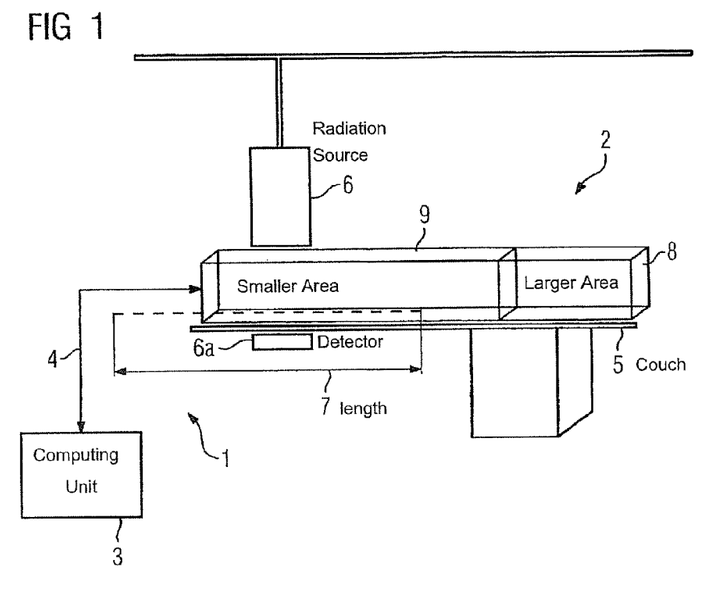
FIG. 1 shows a device according to the invention for position determination.

FIG. 1 shows an inventive device 1 for position determination in conjunction with imaging examination equipment 2. The computing unit 3 of the device 1 for position determination has a memory with examination equipment specific information limiting the spatial position of a medical instrument (not shown here), said information being for the position determination in an examination using the examination equipment 2. The dual arrow 4, which points to the imaging examination equipment 2, indicates this connection.

In the computing unit 3 there is, among other things, collision computer information concerning the dimensions of the patient couch 5 and the movement scope of the radiation source 6 or of the radiation receiver (detector) 6a and the ratios of the dimensions of these. In addition, there is stored in the computing unit 3, a maximum length 7 of a medical instrument the position of which is to be determined. Thus the default of the maximum length 7 of the medical instrument, taking into consideration the dimensions of the patient couch 5 and the extension or the movement scope of the radiation source 6 together produce a limited location area. The larger area 8 shown is a result of allowing for the dimensions of the patient couch 5 and the radiation source 6. This larger area 8 is further limited by the maximum length 7 of the medical instrument, so that the result is the smaller area 9. In this way, according to the invention, the information with respect to the width and length of the patient couch 5 and also the maximum lower position of the patient (not shown here) is taken into account through the height of the patient couch 5, the information with respect to the maximum upper position through the lowest position the radiation source 6 has to reach. This data is stored in the computing unit 3. The computing unit 3 then carries out a position determination that is based on a limited location area and hence the computational effort and consequently the time required to determine the position can be clearly reduced.

Figure 2:
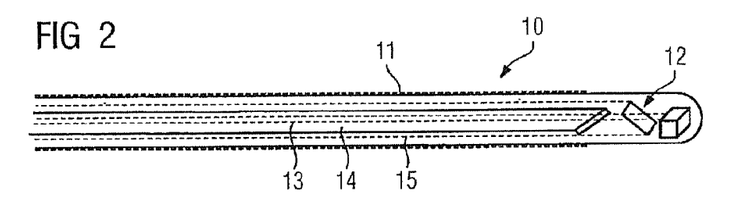
FIG. 2 shows a medical instrument to be located using a device according to the invention.

FIG. 2 shows a medical instrument 10 to be located using a device according to the invention. The medical instrument 10 has a nanocoating 11 on a section and this makes the insertion of the medical instrument 10 into the body of the patient easier and also works as a shield against magnetic interference fields. The medical instrument 10 also has antennae 12 in x-, y- and z-direction in the region of its tip, which antennae form part of an electromagnetic position sensor system and enable the medical instrument 10 to be located in the body of the patient. The system of the antennae 12 and other functional equipment of the medical instrument 10 such as an imaging sensor (not shown) are guided by various signal lines 13 in a lumen 14 and other signal lines 15 outside the lumen 14. The signals picked up or received are forwarded to a computing unit for further processing.

Figure 3:
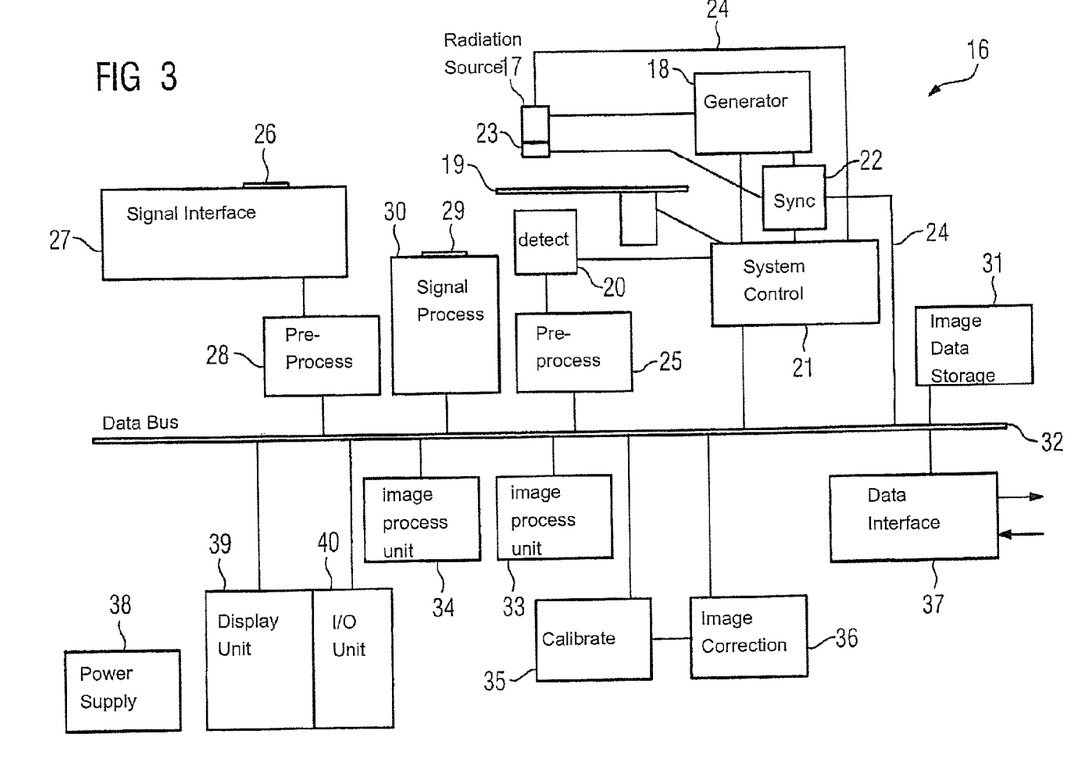
FIG. 3 shows imaging examination equipment according to the invention.

FIG. 3 shows imaging examination equipment 16 according to the invention, in which equipment a radiation source 17 is provided, and whose radiation is generated in a high-voltage generator 18. The radiation is emitted in the direction of a patient (not shown here) on the patient table 19, and the resulting signals are recorded by an X-ray detector 20. Using a system control 21 in conjunction with a synchronization 22, one can synchronize the time intervals or clocking cycles for the radiation transmission or the detector readout and the activation of the magnetic transmitter 23 of the position sensor system. This arrangement is the preferred arrangement. Alternatively, it is possible to arrange the transmitter in the medical instrument 10. Then the receivers would be arranged at the reference number 23. All the signal lines 24 of the examination equipment 16, of which only two, by way of example, have been given reference numbers, have nanocoatings that have a shielding effect against magnetic interference fields.

The X-ray images are pre-processed in a pre-processing unit 25. Likewise the antennae signals from the connection 26 for the magnetic sensors are pre-processed via an associated signal interface 27 in a pre-processing unit 28 for the antennae signals. Further, a connection 29 is provided for physiological sensors, whose signals are input to a physiological signal processing unit 30 for processing. This processing unit processes ECG signals, pulse and respiratory signals and also blood pressure data. Like the image data storage 31, the physiological signal processing unit 30 is linked to a data bus 32, via which are input the data of an image processing unit 33 for medical images and also of an image processing unit 34 for the antennae signals. Further a calibration unit 35 and an image correction unit 36 are linked to the data bus 32.

Thus with the imaging examination equipment 16 according to the invention, the position area of the possible spatial positions of a medical instrument (not shown here) is limited by the system control 21 with the collision computer, while at the same time all the magnetic field changes can be taken into consideration by the image correction unit 36, so that it is possible to position the medical instrument that is provided with position sensors with less effort and greater precision than has been normally possible up until now.

In addition, there is a link via the data bus 32 to an interface 37 for patient and image data. Moreover, a power supply unit 38 is shown and serves to supply power to the imaging examination equipment 16. The magnetic locating images and the medical images taken are shown on the display unit 39 using the input and output unit 40. The image correction unit 36 and the system control 21 synchronize the updating of the images shown on the display unit 39 with the transmission of the radiation by radiation source 17, the activation of the magnetic transmitter 23 and the readout of the X-ray detector 20.

Figure 4:
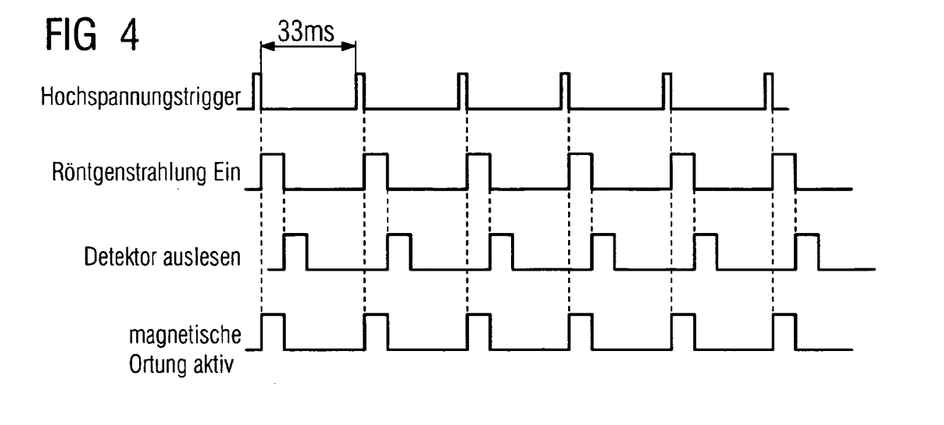
FIG. 4 shows synchronized setting of time intervals or clocking cycles in an X-ray system.

FIG. 4 shows an example for setting time intervals or clocking cycles in an X-ray system. Here, at intervals of 33 ms, a short high voltage pulse is generated as a high voltage trigger for the electronic data processing. Once the trigger pulse has ended, X-ray radiation is emitted, and simultaneously magnetic locating is activated. The X-ray radiation and the magnetic locating are then transmitted or operated for a certain pulse period, which is the same length in both cases. The detector is not readout until the X-ray pulse has ended, which avoids interference. Activating the magnetic locating systems in this way or synchronizing in this way can be used, for example, with detectors based on amorphous silicon, with CCD detectors or television tubes. In the case of amorphous silicon, the influence from magnetic fields is less. Magnetic locating is exact while the X-ray impulse is active, and the detector is read out directly in the connection.

Using the synchronization shown in conjunction with the limitation of the position area, which is provided according to the invention, the image reconstruction can be done faster, magnetic interference fields being taken into consideration in order to increase the precision of the locating.

Figure 5:
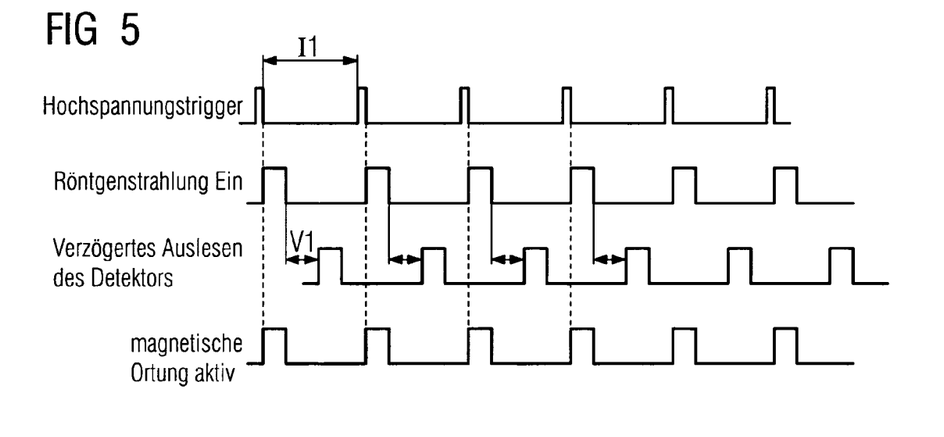
FIG. 5 shows synchronized setting of time intervals or clocking cycles with delayed detector readout.

FIG. 5 shows an example for the synchronized setting of time intervals or clocking cycles with delayed detector readout. Again, a high voltage trigger is generated with an interval I1 of some 10 ms, which the period of time of the radiation transmission follows, corresponding to the period of time in which the magnetic locating is active. As long as the X-ray radiation is being transmitted, the magnetic locating is active. When the radiation ceases, then the magnetic positioning system is also deactivated. The readout of the detector, in this case a CCD detector, follows the switching-off of the X-ray radiation and the deactivation of the magnetic locating systems, with a delay V1 in the range of 10 ms. The delay can be adjustable, e.g. in the range of 1 ms to 20 ms. Here again, interference is avoided by the detector readout being synchronized.

Figure 6:
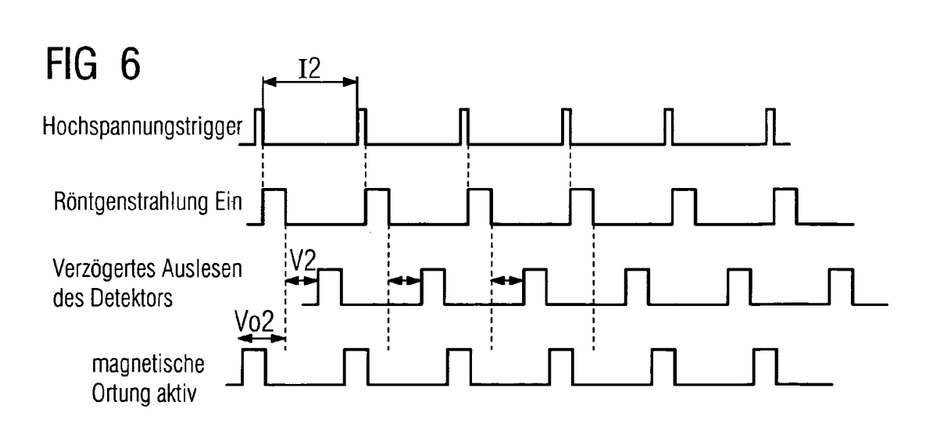
FIG. 6 shows synchronized setting of time intervals or clocking cycles with delayed detector readout and with an advance for the locating.

FIG. 6 shows an example for synchronized setting of time intervals or clocking cycles with delayed detector readout and with an advance for the locating. The creation of the high voltage trigger, that is sent out at intervals I2 in the millisecond range, is followed by the X-ray radiation being switched on. With an adjustable advance Vo2 relating to the end of the radiation transmission, the magnetic locating is already active before the X-ray radiation is switched on, the deactivation occurring while the radiation is still being emitted. The detector, which is an X-ray detector, is read out with such a delay V2 that the readout has ended before the magnetic locating starts again. The cycles for the detector readout or the radiation transmission and the activation of the position sensor system are uniform over the entire duration of the examination.

Figure 7:
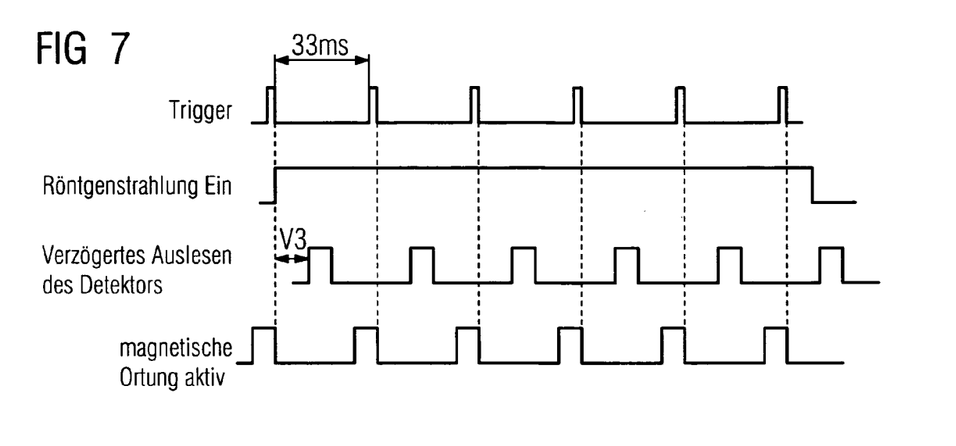
FIG. 7 shows an example for continuous operation of an X-ray source.

By way of example, FIG. 7 shows the continuous operation of an X-ray source, wherein, here again, a trigger is transmitted at intervals of 33 ms. The interval can be set in a range of approx. 10 ms to 100 ms. The magnetic locating is already active before the trigger signal and before switching on of the X-ray radiation that follows the trigger signal. The locating is deactivated when the trigger pulse stops. With respect to the trigger signal, the detector is readout with an adjustable delay V3 at times when the locating is not active. During the continuous transmission of the X-ray radiation, the detector is read out several times, likewise the magnetic locating is activated several times in this period.

Figure 8:
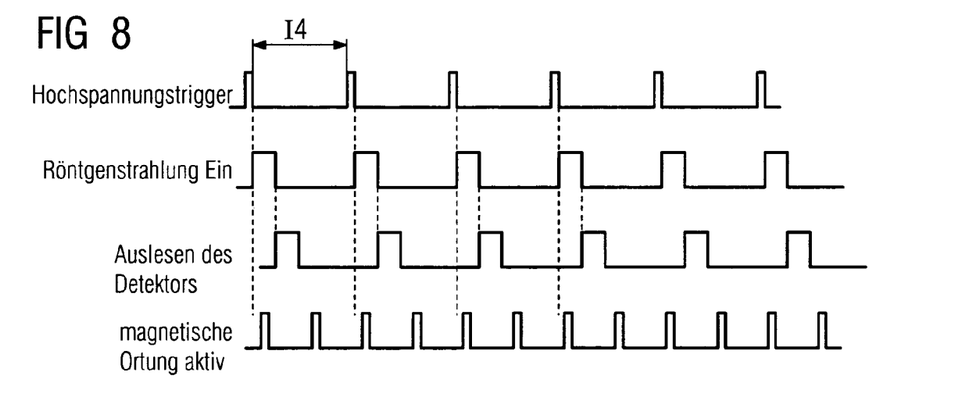
FIG. 8 shows an example for multiple activation of the position sensor system and FIG. 9 shows an example for updating a display output.

FIG. 8 shows an example for multiple activation of the position sensor system with respect to the clocking of the X-ray impulse and of the reading out of the detector. A high voltage trigger is generated with an interval in the range of some 10 ms, that is identified with I4. The pulses of the high voltage trigger are followed by the X-ray radiation, wherein after the end of the radiation transmission the readout of the detector follows without time delay. In contrast the magnetic locating is active more frequently, in such a way that a first locating pulse falls into the area the X-ray radiation falls, while a second locating pulse is arranged between the two X-ray pulses, wherein the locating is active at times when the detector is not being readout.

Figure 9:
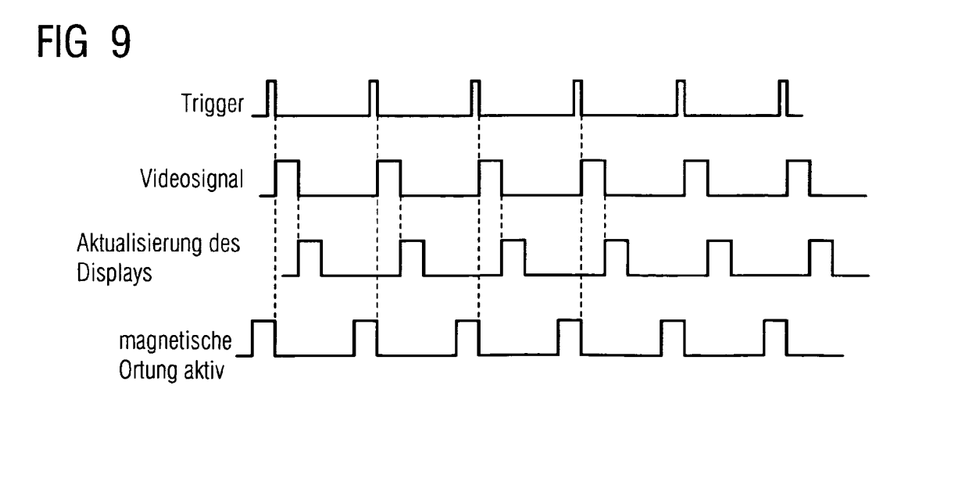

Finally FIG. 9 shows an example for updating a display output, where again the sending of a video signal follows a trigger, wherein the magnetic locating is active in advance of the video signal. The transmission of the video signal is followed by the updating of a display output of the position of the medical instrument or of the images taken. In order to avoid interference from magnetic signals, this updating is synchronized in periods of time when the magnetic locating is not active. Thus, according to the invention, by allowing for all the field changes in the environment of examination equipment, it is possible to increase the precision in locating of a position sensor system with optimal visual presentation.

The invention claimed is:

1. A method for determining a position within a patient of a medical instrument used in a medical imaging examination, comprising:
    (a) retrieving dimensional information comprising a combination of
        (i) dimensions of a table on which a patient is positioned during the medical imaging examination, the dimensions comprising at least a length, a width, and a height of the table top,
        (ii) dimensions of the medical instrument itself wherein an overall length of which corresponds to a maximum length that the medical instrument can be inserted within a patient from an insertion point, and
        (iii) spatial arrangement and positional movement limitations of the medical imaging system, including a lowest height the medical imaging system is capable of reaching;
    (b) calculating from the dimensional information via a computing unit a limited position area representing a possible spatial position of the medical instrument within a patient, wherein,
        (i) a larger limited position area is calculated such that a length and a width are defined by the length and the width of the table, and a lower bound and an upper bound are defined by the height of the table and the lowest height the medical imaging system,
        (ii) the larger limited position area is further refined into a smaller limited position area that does not exceed the overall length that the medical instrument can be inserted within a patient from an insertion point, and
        (iii) wherein each limited position area is calculated without regard to external sensors, transmitters, or receivers positioned about or fixed to a patient to define the limited position area;
    (c) storing in memory the limited position area;
    (d) reducing a search area from an infinite space or an infinite half-space to the limited position area for use during position determination of the medical instrument; and
    (e) determining the position of the medical instrument by searching only within the limited position area calculated from the dimensional information without regard to external sensors, transmitters, or receivers positioned about or fixed to a patient to define the limited position area, thereby reducing computational effort for position determination.

2. The method according to claim 1, wherein the medical instrument comprises a catheter or guide wire having a position sensor device in a region of its tip for determining the position of the medical instrument within the patient and a coating along a section thereof to shield against magnetic interference fields.

3. The method according to claim 1, further comprising retrieving the movement limitations of the medical instrument as part of the dimensional information for calculating the limited position area by a medical equipment collision system.

4. The method according to claim 1, further comprising correcting error based on detected magnetic field changes near the medical instrument.

5. The method according to claim 2, further comprising setting a time interval that achieves a result selected from the group consisting of: a triggering signal, an operation of an imaging unit, an readout of a detector system, an activation of the position sensor device, an updating of an on-screen display of image data, and combinations thereof.

6. The method according to claim 5, wherein a plurality of time intervals that comprise a time delay or time advance are set.

7. The method according to claim 1, wherein imaging examination system is used with the medical instrument that comprises an x-ray source that is operated continuously or pulsed.

8. The method according to claim 2, wherein the position sensor device is activated several times between readout cycles of a detector system.

9. The method according to claim 8 wherein the position sensor device comprises shielding against magnetic fields.

10. The method according to claim 1, further comprising providing a magnetic field detector having signal lines that are magnetically shielded by a film coating, wherein the film coating comprises conductive nanoparticles.

* * * * *